United States Patent [19]

Parslow

[11] 4,018,883
[45] Apr. 19, 1977

[54] THYROXINE ($T_4$) RADIOIMMUNOASSAY

[75] Inventor: Margaret E. Parslow, Rancho Palos Verdes, Calif.

[73] Assignee: Nichols Institute for Endocrinology, San Pedro, Calif.

[22] Filed: Mar. 10, 1975

[21] Appl. No.: 556,930

[52] U.S. Cl. .............................. 424/1; 23/230 B; 424/1.5

[51] Int. Cl.² ................. G01N 33/00; A61K 43/00

[58] Field of Search .............. 424/1, 1.5; 23/230 B, 23/230.6

[56] References Cited

UNITED STATES PATENTS 3,911,096  10/1975  Chopra .................................. 424/1

OTHER PUBLICATIONS

Chopra, Journal of Clinical Endocrinology and Metabolism, vol. 34, 1972, pp. 938–947.
Radioimmunoassay Manual, Nichols Institute for Endocrinology, San Pedro, Calif., Jan. 1974, pp. 15–17.
Desbuquois et al, Journal of Clinical Endocrinology and Metabolism, vol. 33, 1971, pp. 732–738.
Werner et al, Journal of Clinical Endocrinology and Metabolism, vol. 38, 1974, pp. 493–495.

Primary Examiner—Benjamin R. Padgett
Assistant Examiner—Christine M. Nucker
Attorney, Agent, or Firm—Christie, Parker & Hale

[57] ABSTRACT

It has been discovered polyethylene glycol can be added as a separator to the other reagents of a $T_4$ radioimmunoassay of unextracted serum prior to introduction of the serum, without impairing the sensitivity of the measurement. A single, highly stable composite reagent is prepared to measure the concentration of $T_4$ in a measured quantity of human serum; the composite reagent comprises, in freeze dried form, a blocking agent in sufficient quantity to displace essentially all the $T_4$ in the measured quantity of serum bound to TBG, an antibody in sufficient quantity to bind a significant quantity of the $T_4$ in the measured quantity of serum, PEG in sufficient quantity to precipitate essentially all the antibody, and a buffering agent in sufficient quantity to inhibit binding the $T_4$ in the measured quantity of serum to TBP. To run a radioimmunoassay, the human serum being assayed and quantities of standard serums containing known concentrations of $T_4$ are added to a mixture of the composite reagent reconstituted with water and radioactive $T_4$ in sufficient quantity to give a measurable counting rate. After an incubation period, the antibody precipitated by the PEG, including the antibody bound $T_4$, is removed by centrifuging and aspirating the supernatants. The radio activity of the precipitates is then counted to correlate the $T_4$ in the serum being assayed with the standard serums.

24 Claims, No Drawings

THYROXINE ($T_4$) RADIOIMMUNOASSAY

BACKGROUND OF THE INVENTION

This invention relates to the measurement of the concentration of thyroid hormones in human serum and, more particularly, to radioimmunoassay for measurement of thyroxine ($T_4$) in unextracted serum.

One known technique of radioimmunoassay for measurement of $T_4$ in unextracted human serum employs a blocking agent, such as 8-anilino-1-naphthalene-sulfonic acid (ANS), to displace the $T_4$ bound to thyroxine binding globulin (TBG) in the serum being assayed. A mixture of the blocking agent, a $T_4$ binding antibody, radioactive $T_4$ producing a known radioactive count, and buffering ions is added to a phalanx of as many as thirty test tubes containing respectively in duplicate the serum being assayed, a number of standard serums with different known concentrations of $T_4$ for purposes of correlation, and a number of control pool serums. After an incubation period sufficient to allow the reaction of the $T_4$ in the serum and the radioactive $T_4$ with the antibody to proceed substantially to equilibrium, thereby producing antibody bound $T_4$, a percentage of which is radioactive, polyethylene glycol (PEG) is added to the test tubes as a separating agent to precipitate the antibody bound $T_4$. The precipitate in each test tube is removed from the supernatant, its radioactivity is counted, and the radioactivity count of the serum being assayed is correlated with the counts of the standard serums. Since reagents and serum are pipetted three times into a large number of test tubes in the described radioimmunoassay precedure, a substantial amount of laboratory time is expended and the risk of human error is relatively high.

SUMMARY OF THE INVENTION

The invention is based upon the discovery that PEG can be added to the other reagents in a $T_4$ radioimmunoassay prior to the introduction of the serum, without loss of appreciable sensitivity of measurement. Consequently, a substantial amount of laboratory time can be saved and risk of human error can be reduced, because the PEG is added to the remaining reagents before placing them in the test tubes with the serum samples, rather than separately pipetting the PEG into the test tubes after the incubation period of the reagents and the serum samples.

A feature of the invention is a composite reagent for $T_4$ radioimmunoassay comprising a mixture of a blocking agent in sufficient quantity to displace essentially all the $T_4$ in a measured quantity of serum bound to TBG, an antibody in sufficient quantity to bind a significant quantity of the $T_4$ in the measured quantity of serum, PEG in sufficient quantity to precipitate essentially all the antibody, and a buffering agent in sufficient quantity to inhibit binding the $T_4$ in the measured quantity of serum to thyroxine binding preabumin (TBP).

In the preferred embodiment of the composite reagent, the blocking agent is ANS, the buffering agent has a pH of about 8.6, a quantity of gamma globulin is included in the mixture as a visual indicator, and the composite reagent is prepared in freeze dried form. This composite reagent is stable for long periods of time under refrigeration, e.g., for more than six months when stored at a temperature of 4° C.

According to another feature of the invention, a radioimmunoassay method of measuring the concentration of $T_4$ in a measured quantity of human serum comprises the steps of combining together a blocking agent, an antibody, a buffering agent, and PEG to form a mixture, adding to the mixture a measured quantity of human serum to be assayed and radioactive $T_4$ in sufficient quantity to give a measurable counting rate to the mixture, incubating the mixture to allow reaction of the $T_4$ in the serum and the radioactive $T_4$ with the antibody to proceed substantially to equilibrium, removing from the mixture the antibody precipitated by the PEG, including the antibody bound $T_4$, and measuring the quantity of radioactive $T_4$ in the removed precipitate. Preferably, the radioactive $T_4$ is added to the mixture before the mixture is added to the serum containing test tubes. Thus, only two pipetting steps are required in the radioimmunoassay — one to introduce the serum into the test tubes, and one to introduce the mixture containing PEG into the test tubes.

In the preferred embodiment of the method, the composite reagent in freeze dried form of the first described feature is reconstituted with water to form the mixture. The radioactive $T_4$ is added thereto and the resulting mixture is pipetted into test tubes containing the serum samples.

DETAILED DESCRIPTION OF THE PREFERRED EMBODIMENT

It has been discovered polyethylene glycol (PEG) can be added as a separator to the other reagents of a thyroxine ($T_4$) radioimmunoassay of unextracted human serum prior to introduction of the serum, without impairing the sensitivity of the measurement of the concentration of $T_4$ in the serum. Although the PEG precipitates the $T_4$ binding antibody, the reaction of the $T_4$ in the serum and the radioactive $T_4$ with the antibody nevertheless continues. Accordingly, when the serum and the radioactive $T_4$ are added to the reagents, including PEG, the competitive reaction of the $T_4$ in the serum and the radioactive $T_4$ with the antibody proceeds unimpeded, albeit at a somewhat slower rate, to equilibrium. Thus, the percentage of radioactive $T_4$ bound to the antibody in the precipitate after an incubation period is a measure of the concentration of $T_4$ in the human serum.

The first step in the $T_4$ radioimmunoassay procedure is to combine as reagents a blocking agent, radioactive $T_4$, a $T_4$ binding antibody, a separator, and a buffering agent to form a mixture that is added to a number of test tubes containing a measured quantity of human serum samples to be assayed and standard serum samples having known $T_4$ concentrations. Only two pipetting steps are required with respect to each test tube — one to introduce the serum sample into the test tube, and one to introduce the mixture into the test tube.

The blocking agent is preferably 8-anilino-1-napthalene-sulfonic acid (ANS), but a number of other known blocking agents such as 3-(4 anilino-1-napthylazo) 2,7-napthalene disulfonic acid (ANNDS) or 2, 4 6-trinitro benzene sulfonic acid (TNBS) could also be used as blocking agents. In any case, it is important that the blocking agent be present in sufficient quantity to displace all the $T_4$ bound to thyroxine binding globulin (TBG) in the serum and free it for competitive reaction with radioactive $T_4$ for binding to the $T_4$ antibody. In the case of ANS, 100 micrograms of ANS will displace 18 nanograms of $T_4$; sufficient ANS is employed to displace a greater amount of $T_4$ than could be expected to be found in the serum sample being assayed so as to provide a safety factor.

A sufficient quantity of radioactive $T_4$, e.g., $T_4$ labeled with iodine 125, is added to the mixture to provide a measurable counting rate in the individual test tubes after reaction with the $T_4$ antibody, e.g., 2000 to 6000 counts per minute. However, the quantity of radioactive $T_4$ depends upon the sensitivity of the counting equipment, the more sensitive the equipment the less radioactive the $T_4$ must be to give a measurable counting rate.

The $T_4$ antibody may be obtained from a rabbit immunized with normal human thyroglobulin (Tg), as described by Chopra et al, J. Clinical Endocrinology and Metabolism 32:299. The quantity of the $T_4$ antibody used, which will vary from batch to batch, is sufficient to bind between 35% and 50% of the radioactive $T_4$ in the absence of any non-radioactive $T_4$, i.e., in the absence of serum. If too much $T_4$ antibody is used, there will not be a satisfactory competitive reaction between $T_4$ in the serum and radioactive $T_4$ for the $T_4$ antibody.

The quantity of $T_4$ antibody is normally not large enough to provide a visible button in the individual test tubes. Thus, gamma globulin is added to the mixture as a visual indicator, i.e., to provide enough precipitate so a visual button is present in the individual test tubes after centrifuging and aspirating the supernatant. The gamma globulin is otherwise a neutral constituent in the mixture because it does not bind $T_4$ or react with any other constituents, except the separator.

Polyethylene glycol (PEG), such as Carbowax 6000, is employed as a separator to precipitate the $T_4$ antibody and the gamma globulin. It is important that enough PEG to precipitate all the $T_4$ antibody and gamma globulin be used. A relatively large quantity of PEG, e.g., 17% by weight of the mixture or more is required for this purpose.

The buffering agent is employed to inhibit the binding of $T_4$ to thyroxine binding prealbumin (TBP). Generally, the mixture is buffered by a buffering agent such as barbital to a pH in the range between 6.8 and 9.6.

An important feature of the invention is the production of a composite reagent comprising the blocking agent, the $T_4$ antibody with gamma globulin if necessary, the separator, and the buffering agent. In freeze dried form, this composite reagent is stable for more than six months. This freeze dried composite reagent, a thyroxine standard, i.e., a standard serum containing a known concentration of $T_4$ in freeze dried form, and radioactive $T_4$ can be furnished to medical laboratories as a complete kit that permits the laboratories to carry out $T_4$ radioimmunoassays without having to mix the reagents themselves. To form the mixture described above, the composite reagent is reconstituted by adding it to a measured quantity of water and then introducing radioactive $T_4$. Standard serum samples having different known $T_4$ concentrations are produced by reconstituting the thyroxine standard by adding water to it and diluting the reconstituted standard in different ratios.

If desired, the radioactive $T_4$ could be mixed with the other constituents as part of the freeze dried composite reagent. However, since iodine-125 has a half-life of about 60 days, this would severely limit the shelf life of the composite reagent. Thus, in most cases, it is preferable to provide the freeze dried composite reagent, without radioactive $T_4$, as one constituent and radioactive $T_4$ as a separate constituent in a $T_4$ radioimmunoassay kit.

The second step in the $T_4$ radioimmunoassay procedure is to pipette a measured quantity of the standard serum samples and the serum sample being assayed into individual test tubes.

The third step in the $T_4$ radioimmunoassay procedure is to pipette a measured quantity of the reconstituted composite reagent with radioactive $T_4$ into the individual test tubes containing the serum samples.

The fourth step in the $T_4$ radioimmunoassay procedure is to mix the contents of all the test tubes thoroughly and incubate the contents of all the test tubes until the reaction of the $T_4$ in the serum samples and the radioactive $T_4$ with the $T_4$ antibody proceeds substantially to equilibrium, so a percentage of the $T_4$ in the serum samples replaces the radioactive $T_4$ bound to the $T_4$ antibody in the precipitate.

The fifth step in the $T_4$ radioimmunoassay procedure is to remove the precipitate from the remainder of the contents of all the test tubes. This is conventionally done by centrifuging the contents of the individual test tubes and then aspirating the supernatants, leaving a precipitate button at the bottom of each test tube.

The sixth step in the $T_4$ radioimmunoassay procedure is to count the radioactivity of the precipitate button in each tube.

The seventh and final step in the $T_4$ radioimmunoassay procedure is to prepare a graph of the radioactivity counts of the different standard serum samples as a function of the respective known $T_4$ concentrations and to correlate the radioactivity count of the serum sample being assayed with the graph to determine its $T_4$ concentration.

METHOD OF PRODUCING COMPOSITE REAGENT — EXAMPLE

1. One pkg. of Beckman B-2 buffer was dissolved in 800 milliliters of deionized water. the buffer was placed in a volumetric flask and the volume was brought up to 1 liter by addition of more deionized water. The resulting buffering agent had a pH of 8.6 and an ionic strength of 0.075 moles. This buffering agent is stable for two months at a temperature of 4° C and is used for a number of assays until consumed.

2. 70 milliliters of the buffering agent described in step 1 above, was poured into a beaker.

3. 30 milligrams of 8-anilino-1-napthalene-sulfonic acid sodium salt (ANS), technical grade, obtained from K & K Laboratories, Hollywood, California, and 300 milligrams of gamma globulin, bovine Fraction II, obtained from Nutritional Biochemicals, Cleveland, Ohio, were dissolved in the 70 milliliters of buffering agent.

4. 17.5 grams of PEG having a molecular weight between 6000 and 7500, commercially called Carbowax 6000, obtained from Dow Chemical Company, was added slowly to the mixture to obtain a thick slurry as the PEG precipitates the gamma globulin.

5. 0.334 microliters of $T_4$ antibody obtained from a rabbit immunized with normal human thyroglobulin, as described in the above Chopra et al article, was added to the mixture. (The exact quantity of the $T_4$ antibody needed to bind the desired percentage, e.g., 35–50%, of the radioactive $T_4$ in the absence of serum varies from batch to batch.)

6. The mixture was mixed for a few minutes and the final volume was brought up to 100 milliliters by adding more of the buffering agent described in step 1 above.

7. The mixture described in step 6 above was then freeze dried by conventional techniques. The resulting freeze dried mixture is a composite reagent that is stable for a long period of time, e.g., more than 6 months stored at a temperature of 4° C.

$T_4$ RADIOIMMUNOASSAY METHOD — EXAMPLE I

1. A buffering agent, gamma globulin, ANS, PEG, and a $T_4$ antibody were mixed in the manner described above in steps 1 through 6 under METHOD OF PRODUCING COMPOSITE REAGENT — EXAMPLE to produce a 100 milliliter mixture.

2. 40 nanograms of iodine-125 labeled thyroxine having a specific activity of 100 millicuries per milligram, obtained from Industrial Nuclear Corporation, St. Louis, Missouri, were added to the 100 milliliter mixture. This provided a counting rate of about 20,000 counts per minute per 0.5 milliliters with a counter having an efficiency of about 50%.

3. The thyroxine standard sold by the Nichols Institute for Endocrinology, 3100 South Beacon St., San Pedro, Calif., was reconstituted with 3.8 milliliters of deionized water in a flask to provide a standard serum having 20.0 micrograms of $T_4$ per 100 milliliters of serum.

4. The reconstituted thyroxine standard serum was diluted with deionized water in different ratios to obtain six other standards as follows:

| Dilution | Value ($\mu$g/100ml) | Dilutions Instructions |
| --- | --- | --- |
| As reconstituted | 20.0 | 1.0 ml standard as reconstituted |
| 1:1.3 | 15.4 | 1.0 ml standard + 0.3 ml deionized water |
| 1:1.5 | 13.3 | 1.0 ml standard + 0.5 ml deionized water |
| 1:2 | 10.0 | 1.0 ml standard + 1.0 ml deionized water |
| 1:3 | 6.7 | 0.5 ml of 1:1.5 + 0.5 ml deionized water |
| 1:4 | 5.0 | 1.0 ml of 1:2 + 1 ml deionized water |
| 1:8 | 2.5 | 1.0 ml of 1:4 + 1 ml deionized water |

5. 0.01 milliliters of the seven standard serum samples were pipetted in duplicate respectively into 14 test tubes.

6. 0.01 milliliters of the serum sample being assayed in duplicate were pipetted respectively into 2 test tubes. (In accordance with standard practice plasma controls from a low pool, normal pool, and high pool were also pipetted into respective test tubes for purposes of quality control.)

7. 0.5 milliliters of the mixture obtained from step 2 above, containing the radioactive $T_4$ was pipetted into all the test tubes and also into several empty test tubes to determine the total radioactivity count in the absence of serum and thus provide the radioactivity count representing 100% of radioactive bound $T_4$. During this procedure, the container for the mixture was swirled continuously so the precipitate remained distributed throughout the mixture, i.e., so the precipitate did not settle.

8. The contents of all the test tubes were mixed thoroughly for 5 to 10 seconds by a vortex mixer and incubated at room temperature for 2 hours.

9. After incubation, all the tubes were spun in a refrigerated centrifuge at a temperature of 2° to 6° C for 20 to 30 minutes at 2000 RPM. (Before centrifuging, the tubes could be stored up to 12 hours at a temperature of 4° C after the incubation period at room temperature is completed, without impairing the radioimmunoassay results.)

10. The supernants were aspirated from all the test tubes with a vacuum pump immediately after centrifuging and the excess PEG was carefully cleaned off the sides of each test tube, leaving the precipitate button intact.

11. The radioactivity of the precipitate button in each test tube was counted.

12. A graph was prepared from the radioactivity counts of the standard serum samples. The percentage of bound radioactive $T_4$ was the ordinate and the $T_4$ concentration in micrograms per hundred milliliters was the abscissa of the graph. The radioactivity count in the test tubes without serum was taken as 100% bound, and the percentage bound in the standard serum samples was given by the ratio of the radioactivity count of such samples to the radioactivity count of the test tubes without serum. A typical graph of this type is disclosed on page 17 of the Radioimmunoassay Manual, published by Nichols Institute for Endocrinology, 3100 South Beacon St., San Pedro, Calif., 90731, January 1974.

13. The radioactivity count of the serum sample being assayed was correlated with the standard serum samples by reading from the graph the $T_4$ concentration corresponding to the percentage of bound radioactive $T_4$ in the precipitate button of the serum sample being assayed, as given by its radioactivity count.

$T_4$ RADIOIMMUNOASSAY METHOD — EXAMPLE II

1. The freeze dried composite reagent resulting from step 7 under METHOD OF PRODUCING COMPOSITE REAGENT — EXAMPLE, was reconstituted with 100 milliliters of deionized water and mixed for about 15 minutes.

2. 40 nanograms of iodine-125 labeled thyroxine having a specific activity of 100 millicuries per milligram obtained from Industrial Nuclear Corporation, St. Louis, Missouri, were added to the 100 milliliter mixture. This provided a counting rate of about 20,000 counts per minute per 0.5 milliliters with a counter having an efficiency of about 50%.

3. Steps 3 through 13 described above under $T_4$ RADIOIMMUNOASSAY METHOD — EXAMPLE I, were carried out to measure the $T_4$ concentration in a serum to be assayed.

The described embodiments of the invention are only considered to be preferred and illustrative of the inventive concept; the scope of the invention is not to be restricted to such embodiments. Various and numerous other arrangements may be devised by one skilled in the art without departing from the spirit and scope of this invention. For example, many other types of blocking agents could be employed, the invention may be applicable to $T_3$ radioimmunoassays and other types of separators may possibly also be used to practice the invention. Rather than count the radioactivity of the precipitate, i.e. the bound radioactive $T_4$, the radioactivity of the supernatant, i.e. the unbound radioactive $T_4$, could be counted to measure the $T_4$ concentration of the serum.

What is claimed is:

1. A composite reagent for a radioimmunoassay to measure the concentration of thyroxine ($T_4$) in a measured quantity of human serum, the reagent comprising in the absence of non-radioactive $T_4$:
   a blocking agent in sufficient quantity to displace essentially all of the $T_4$ in the measured quantity of serum bound to thyroxine-binding globulin (TBG);
   an antibody in sufficient quantity to bind a significant quantity of the $T_4$ in the measured quantity of serum;
   polyethylene glycol (PEG) in sufficient quantity to precipitate essentially all the antibody; and
   a buffering agent in sufficient quantity to inhibit binding the $T_4$ in the measured quantity of serum to thyroxine-binding prealbumin.

2. The reagent of claim 1, in which the blocking agent is 8-anilino-1-naphthaline-sulfonic acid (ANS).

3. The reagent of claim 2, in which the buffering agent has a pH of about 8.6.

4. The reagent of claim 3, additionally comprising a sufficient quantity of gamma globulin to provide a visual indicator.

5. The reagent of claim 4, additionally comprising radioactive $T_4$.

6. The reagent of claim 5, in a freeze dried form.

7. The reagent of claim 1, in which the buffering agent has a pH of about 8.6.

8. The reagent of claim 1, additionally comprising a sufficient quantity of gamma globulin to provide a visual indicator.

9. The reagent of claim 1, additionally comprising radioactive $T_4$.

10. The reagent of claim 1, in a freeze dried form.

11. The method of preparing a composite reagent for a radioimmunoassay to measure the concentration of thyroxine ($T_4$) in a measured quantity of serum, the method comprising the following steps in the order recited:
    dissolving in an aqueous buffer solution having a pH of about 8.6 sufficient gamma globulin to provide a visible precipitate after centrifusion and supernatant aspiration and sufficient 8-anilino-1-naphthalene-sulfonic acid (ANS) to displace all the $T_4$ bound to thyroxine binding globulin in the measured quantity of serum;
    slowly adding sufficient polyethylene glycol (PEG) to precipitate substantially all the gamma globulin, thereby producing a thick slurry;
    adding to the slurry an antibody capable of binding a significant quantity of $T_4$; and
    thoroughly mixing the recited ingredients.

12. The method of claim 11, comprising the additional step of freeze drying the mixed ingredients.

13. The method of claim 11, comprising the additional step of adding a measurable amount of radioactive $T_4$ to the mixed ingredients in the absence of human serum.

14. A method of measuring the concentration of thyroxine ($T_4$) in a measured quantity of human serum, the method comprising the steps of:
    combining the following to form a mixture:
      a blocking agent in a quantity sufficient to displace essentially all the $T_4$ in the measured amount of human serum from thyroxine binding globulin (TBG);
      an antibody in sufficient quantity to bind a significant quantity of the $T_4$ in the measured quantity of serum;
      polyethylene glycol (PEG) in sufficient quantity to precipitate essentially all the antibody; and
      a buffering agent in sufficient quantity to inhibit binding the $T_4$ in the measured quantity of serum to thyroxinebinding prealbumin;
    adding the mixture to the measured quantity of human serum and radioactive $T_4$ in sufficient quantity to give a measurable counting rate;
    incubating the serum and radioactive $T_4$ with the mixture added to allow reaction of the $T_4$ in the serum and the radioactive $T_4$ with the antibody to proceed substantially to equilibrium, thereby producing antibody bound $T_4$, a percentage of which is radioactive;
    removing the antibody precipitated by the PEG including the antibody bound $T_4$ from the supernatant; and
    measuring the quantity of radioactive $T_4$ in the removed precipitate or the supernatant.

15. The method of claim 14, in which the step of adding the mixture to the measured quantity of human serum and radioactive $T_4$ comprises the steps of:
    adding the radioactive $T_4$ to the mixture before adding the mixture to the measured quantity of human serum;
    pipetting the measured quantity of human serum into a test tube; and
    pipetting a measured quantity of the mixture including radioactive $T_4$ into the test tube.

16. The method of claim 15, in which the measuring step comprises the steps of:
    pipetting into a plurality of test tubes measured quantities of standard human serum samples having different known concentrations of $T_4$;
    pipetting into the test tubes measured quantities of the mixture including radioactive $T_4$;
    incubating the standard serum samples and radioactive $T_4$ with the mixture added to allow reaction of the $T_4$ in the standard serum samples and the radioactive $T_4$ with the antibody to proceed substantially to equilibrium, thereby producing antibody bound $T_4$ a percentage of which is radioactive;
    removing the antibody precipitated by the PEG including the antibody bound $T_4$ of the standard serum samples;
    counting the radioactivity in the precipitate including the antibody bound $T_4$ of the measured quantity of human serum being assayed;
    counting the radioactivity of the precipitate including the antibody bound $T_4$ of the standard serum samples; and
    correlating the count of the serum being assayed with the counts of the standard serum samples.

17. The method of claim 14, in which gamma globulin is combined in the mixture in sufficient quantity to provide a precipitate visible to the human eye.

18. The method of claim 14, in which the removing step comprises the steps of:
    centrifuging the serum and radioactive $T_4$ with the mixture added; and
    aspirating the supernatants.

19. The method of claim 14, in which the blocking agent comprises 8-anilino-1-naphthalene-sulfonic acid (ANS).

20. The method of claim 14, in which the radioactive $T_4$ in the mixture is approximately 0.2 nanograms per 0.5 milliliters of the mixture and the radioactivity is approximately 100 millicures per milligram of $T_4$.

21. The method of claim 20, in which the mixture contains approximately 17.5 percent by weight of PEG and 3 percent by weight of gamma globulin.

22. The method of claim 21, in which the mixture contains the antibody in sufficient quantity to bind between 35% and 50% of the radioactive $T_4$.

23. The method of claim 22, in which the mixture contains as a blocking agent approximately 0.03 percent of 8-anilino-1-naphthalene-sulfonic acid (ANS) by weight.

24. The method of claim 11, in which the gamma globulin and the ANS in the dissolving step are approximately in the ratio of 10:1.

* * * * *